(12) United States Patent
Gilkerson et al.

(10) Patent No.: US 7,202,240 B2
(45) Date of Patent: Apr. 10, 2007

(54) ANTIFUNGAL 4-SUBSTITUTED 5,6-DIHYDRO-4H-PYRROLO[1,2-A][1,4] BENZODIAZEPINES

(75) Inventors: Terence Gilkerson, Canterbury (GB); Roger John Nash, Ashford (GB); Jozel Frans Elisabetha Van Gestel, Vosselaar (BE); Lieven Meerpoel, Beerse (BE)

(73) Assignee: Janssen Pharmaceutica N.V. (BE)

( * ) Notice: Subject to any disclaimer, the term of this patent is extended or adjusted under 35 U.S.C. 154(b) by 232 days.

(21) Appl. No.: 10/399,596

(22) PCT Filed: Oct. 17, 2001

(86) PCT No.: PCT/EP01/12287

§ 371 (c)(1),
(2), (4) Date: Feb. 4, 2004

(87) PCT Pub. No.: WO02/34752

PCT Pub. Date: May 2, 2002

(65) Prior Publication Data
US 2004/0266756 A1 Dec. 30, 2004

(30) Foreign Application Priority Data
Oct. 23, 2000 (EP) .................. 00203726

(51) Int. Cl.
*A61K 31/55* (2006.01)
*A61P 31/10* (2006.01)
*C07D 487/04* (2006.01)

(52) U.S. Cl. ...................... 514/220; 540/561
(58) Field of Classification Search ................ 514/220; 540/561
See application file for complete search history.

(56) References Cited

OTHER PUBLICATIONS

F. Corelli et al., "Sistemi eterociclici", Farmaco Ed. Sci., vol. 39, No. 8, pp. 707-717 (1984).

S. Raines et al., "Mannich Reactions. Synthesis of 4,5-Dihydropyrrolo[1,2-α] quinoxalines, 2,3,4,5-Tetrahydro-1*H*-pyrrolo[1,2-α][1,4] diazepines and 5,6-Dihydro-4*H*-pyrrolo[1,2-α] [1,4] benzodiazepines", J. Heterocycl. Chem., vol. 13, pp. 711-716 (1976).

G.W.H. Cheeseman et al., "Further Cyclisation Reactions of 1-Arylpyrroles", J. Chem. Soc., pp. 2732-2734 (1971).

S. Vomero et al., "Ricerche su composti eterociclici azotati", Farmaco Ed. Sci., vol. 35, No. 2, pp. 110-119 (1980).

PCT International Search Report, dated Feb. 20, 2002, for PCT Int'l Pat. No. WO02/34752.

Corelli, F. et al., "Heterocyclic Systems", *Sistemi Eterociclici*, Institute of Pharmaceutical Chemistry and Toxicology, 1984, 707-717, Full English Language Translation from Italian.

Vomero, S. et al., "Research in Relation to Nitrogenated Heterocyclic Systems", *Institute of Pharmaceutical Chemistry and Toxicology*, 1980, 110-119, Full English Language Translation from Italian.

*Primary Examiner*—Brenda Coleman

(57) ABSTRACT

The present invention concerns compounds for use as a medicine having the formula (I), the N-oxide forms, the salts, the quaternary amines and stereochemically isomeric forms thereof, wherein $R^1$ represents hydrogen, $C_{1-6}$ alkyl, $C_{1-4}$alkylthio, $C_{1-4}$alkyloxy, or halo; $R^2$ represents hydrogen or $C_{1-6}$alkyl; $R^3$ represents phenyl substituted with halo, cyano, $C_{1-4}$alkyloxy, $C_{1-4}$alkylthio, $C_{1-6}$alkyl, halo$C_{1-6}$alkyl; 2-thienyl; or 3-thienyl, $R^4$ represents hydrogen; or $R^2$ and $R^4$ form an extra bond, which are active against dermatophytes, and their preparation; it further relates to compositions comprising them, as well as their use as a medicine.

7 Claims, No Drawings

ANTIFUNGAL 4-SUBSTITUTED 5,6-DIHYDRO-4H-PYRROLO[1,2-A][1,4] BENZODIAZEPINES

CROSS REFERENCE TO RELATED APPLICATIONS

This application is a National Stage application under 35 U.S.C. 371 of Application No. PCT/EP01/12287 filed Oct. 17, 2001, which claims priority from EP 00203726.5, filed Oct. 23, 2000.

The present invention is concerned with a new class of antifungals active mainly against dermatophytes, and their preparation; it further relates to compositions comprising them, as well as their use as a medicine.

5,6-Dihydro-4H-pyrrolo[1,2-a][1,4]benzodiazepines have been described in J. Chem. Soc.(C), 2732–2734 (1971); J. Heterocyclic Chem., 13, 711–716 (1976); and J. Heterocyclic Chem., 16, 241–244 (1979); no biological activities were reported in any of these references.

The present invention concerns compounds for use as a medicine having the formula

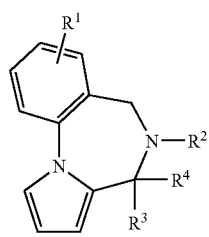
(I)

the N-oxide forms, the salts, the quaternary amines and stereochemically isomeric forms thereof, wherein
$R^1$ represents hydrogen, $C_{1-6}$alkyl, $C_{1-4}$alkylthio, $C_{1-4}$alkyloxy, or halo;
$R^2$ represents hydrogen or $C_{1-6}$alkyl;
$R^3$ represents phenyl substituted with halo, cyano, $C_{1-4}$alkyloxy, $C_{1-4}$alkylthio, $C_{1-6}$alkyl, halo$C_{1-6}$alkyl; 2-thienyl; or 3-thienyl; and
$R^4$ is hydrogen; or
$R^2$ and $R^4$ form an extra bond.

The compounds of formula (I) are novel provided that $R^3$ is not 4-methylphenyl, 4-methoxyphenyl or 4-isopropylphenyl when $R^1$, $R^2$ and $R^4$ are hydrogen; and $R^3$ is not 4-methoxyphenyl, 4-ethylphenyl or 3-trifluorophenyl when $R^1$ is 7-chloro, and $R^2$ and $R^4$ are hydrogen.

The atoms in the tricyclic system are numbered as shown in the following formula (II).

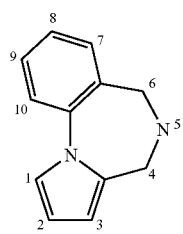
(II)

As used in the foregoing definitions and hereinafter halo defines fluoro, chloro, bromo and iodo; $C_{1-4}$alkyl as a group or part of a group encompasses the straight and branched chain saturated hydrocarbon radicals having from 1 to 4 carbon atoms such as, for example, methyl, ethyl, propyl, butyl and the like; $C_{1-6}$alkyl as a group or part of a group encompasses the straight and branched chain saturated hydrocarbon radicals as defined in $C_{1-4}$alkyl as well as the higher homologues thereof containing 5 or 6 carbon atoms such as, for example, pentyl or hexyl; halo$C_{1-6}$alkyl defines $C_{1-6}$alkyl wherein at least one hydrogen atom is replaced by a halo atom up to all hydrogen atoms being replaced by halo atoms, such as for example, fluoromethyl, difluoromethyl, or trifluoromethyl.

For therapeutic use, salts of the compounds of formula (I) are those wherein the counterion is pharmaceutically acceptable. However, salts of acids which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term addition salt also comprises the hydrates and solvent addition forms which the compounds of formula (I) are able to form. Examples of such forms are e.g., hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be made using ion exchange resin columns.

The term "stereochemically isomeric forms" as used hereinbefore defines all the possible stereoisomeric forms in which the compounds of formula (I) exist, thus, also including all enantiomers, enantiomeric mixtures and diastereomeric mixtures. Unless otherwise mentioned or indicated, the chemical designation of compounds denotes the mixture of all possible stereoisomeric forms, said mixtures containing all diastereomers and enantiomers of the basic molecular structure. The same applies to the intermediates as described herein, used to prepare end products of formula (I).

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' being equivalent to 'chirally pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

The compounds of Formula (I), wherein R4 is hydrogen, all contain at least 1 asymmetric center which may have the R- or S-configuration. As used herein, the stereochemical descriptors denoting the stereochemical configuration of the asymmetric center are in accordance with Chemical Abstracts nomenclature.

Of some compounds of formula (I) and of intermediates used in their preparation, the absolute stereochemical configuration was not experimentally determined. In those cases the stereoisomeric form which was first isolated is designated as "A" and the second as "B", without further reference to the actual stereochemical configuration. However, said "A" and "B" stereoisomeric forms can be unambiguously characterized by for instance their optical rotation in case "A" and "B" have an enantiomeric relationship. A person skilled in the art is able to determine the absolute configuration of such compounds using art-known methods such as, for example, X-ray diffraction.

The N-oxide forms of the present compounds are meant to comprise the compounds of formula (I) wherein one or several nitrogen atoms are oxidized to the so-called N-oxide.

Whenever used hereinafter, the term "compounds of formula (I)" is meant to include N-oxide forms, salts, quaternary amines and stereochemically isomeric forms. Of special interest are those compounds of formula (I) which are stereochemically pure.

Also of interest are compounds wherein
$R^1$ represents hydrogen, $C_{1-6}$alkyl or halo;
$R^2$ represents hydrogen or $C_{1-6}$alkyl;
$R^3$ represents phenyl substituted with halo, cyano, $C_{1-4}$alkyloxy, $C_{1-6}$alkyl, halo$C_{1-6}$alkyl; 2-thienyl or 3-thienyl, and
$R^4$ represents hydrogen; or $R^2$ and $R^4$ form an extra bond.

An interesting group of compounds are those compounds of formula (I) wherein
$R^1$ represents hydrogen or halo;
$R^2$ represents hydrogen or $C_{1-6}$alkyl;
$R^3$ represents phenyl substituted with $C_{1-6}$alkyl;
$R^4$ represents hydrogen; or $R^2$ and $R^4$ form an extra bond.

Especially interesting are those compounds of formula (I) wherein
$R^1$ represents hydrogen, 7-chloro, 7-fluoro or 9-chloro;
$R^2$ represents hydrogen; and
$R^3$ represents phenyl substituted with $C_{1-6}$alkyl.
$R^4$ represents hydrogen; or $R^2$ and $R^4$ form an extra bond.

Most interesting are compounds (2), (21), (22), (23) and (24).

The compounds of the present invention can be prepared according to reaction scheme 1.

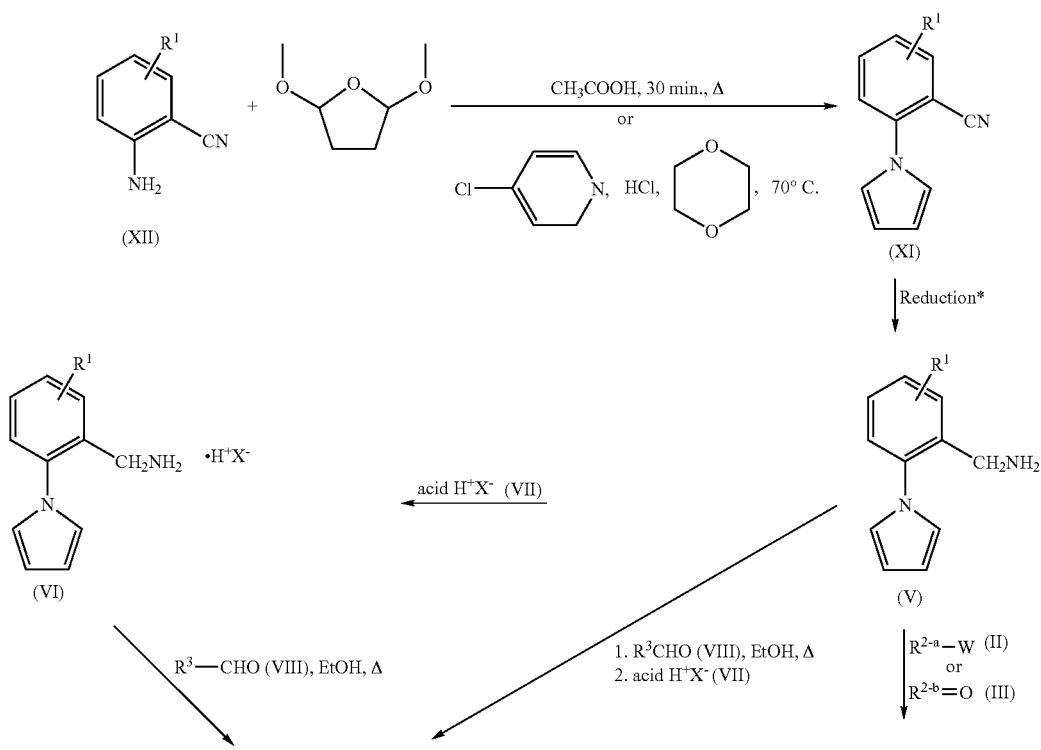

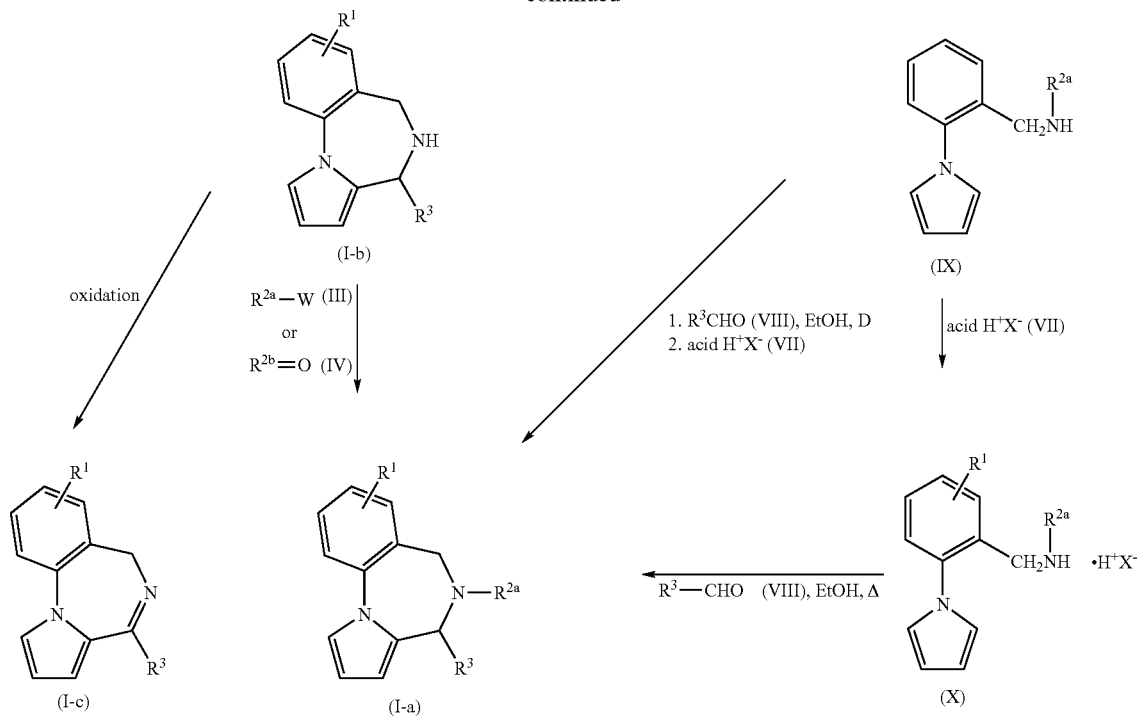

The compounds of formula (I) wherein $R^2$ represents $C_{1-6}$alkyl, said compounds being represented by formula (I-a) wherein $R^{2a}$ is $C_{1-6}$alkyl, can be prepared from the compounds represented by formula (I-b), following art-known N-alkylation and reductive amination reactions.

The N-alkylation reactions are conducted by reacting a compound of formula (I-b) with an alkylating agent $R^{2a}$—W (III) wherein W is a leaving group such as halo, e.g. chloro, bromo or iodo, or a sulfonyloxy group, e.g. methanesulfonyloxy (mesylate) or 4-methylbenzenesulfonyloxy (tosylate) in an appropriate solvent such as an alkanol, e.g. methanol, ethanol, isopropanol; a ketone, e.g. acetone or methylisopropylketone; a dipolar aprotic solvent, e.g. N,N-dimethylformamide, N,N-dimethylacetamide; in the presence of a base such as an alkali metal hydroxide or carbonate, e.g. sodium or potassium hydroxide, or sodium or potassium carbonate. The N-alkylation reaction can also be conducted by reacting a compound of formula (I-b) with a dialkylsulphate, e.g. dimethylsulphate in water or a mixture of water and an alkanol in the presence of a base such as sodium bicarbonate. The reaction rate can be enhanced by stirring and heating the reaction mixture, and—if required—by catalyzing the N-alkylation reaction with an appropriate catalyst such as potassium iodide.

Reductive amination reactions can be conducted by reacting a compound of formula (I-a) with an aldehyde or ketone of formula $R^{2-b}$=O (IV) wherein $R^{2-b}$ represents a $C_{1-6}$alkanediyl radical and =O represents an oxo-group, in an appropriate solvent such as an alkanol, e.g. methanol, ethanol, isopropanol; a dipolar aprotic solvent, e.g. N,N-dimethylformamide, N,N-dimethylacetamide; in the presence of a reducing agent such as sodiumborohydride, or in the presence of hydrogen and a catalyst such as palladium. The reaction rate can be enhanced by stirring and heating the reaction mixture.

The compounds of formula (I) wherein $R^2$ and $R^4$ together form an extra bond, said compounds being represented by formula (I-c), can be prepared from the compounds represented by the formula (I-b), following art-known amine to imine oxidation reactions. These oxidation reactions may be conducted by reacting a compound of formula (I-b) with an oxidant such as, for example, lead tetraacetate or manganese dioxide, in a reaction inert solvent such as a halogenated hydrocarbon e.g. dichloromethane or trichloromethane. The reaction rate can be enhanced by stirring and optionally heating the reaction mixture.

The compounds of formula (I-b) can be prepared from a 1-(2-aminomethylphenyl)-pyrrole (V) by converting it in a salt (VI) by reaction with an acid $H^+X^-$ (VII), and reacting said salt (VI) with an aldehyde of formula (VIII) in an appropriate solvent such as an alkanol, e.g. methanol, ethanol, isopropanol, at an elevated temperature, preferably at reflux temperature.

Alternatively, the intermediate of formula (V) may be reacted first with the aldehyde $R^3$—CHO (VIII) and the thus formed intermediate imine may be cyclized in the presence of an acid $H^+X^-$ (VII) to a compound of formula (I-b).

Yet another alternative comprises N-alkylating the intermediate of formula (V) with a reagent $R^{2a}$—W (III) or $R^{2b}$=O (IV) under the conditions described before to yield an amine of formula (IX) which is further converted to a salt form (X) and reacted with an aldehyde (VIII) as described before.

The intermediate of formula (V) is prepared by reducing a 1-(2-cyanophenyl)pyrrole (XI). Four different procedures may be used to reduce the nitrile funtion.
1. LiAlH$_4$/THF [S. Raines, S. Y. Chai and F. P. Palopoli; J. Heterocyclic Chem., 13, 711–716 (1976)]
2. i. sodium bis(2-methoxyethoxy)aluminate (Red-Al®) 70% w/w Toluene, RT;

ii. NaOH 10%, RT [G. W. H. Cheeseman and S. G. Greenberg; J. Heterocyclic Chem., 16, 241–244(1979)]

3. i. KBH$_4$/CF$_3$COOH, THF; ii. H$_2$O; iii. HCl [P. Trinka, P. Slégel and J. Reiter; J. Prakt. Chem., 338, 675–678 (1996)]

4. RaNi/H$_2$

The intermediate of formula (XI) in turn, is prepared by treating a 2-aminobenzonitrile (XII) with 2,5-dimethoxyfuran in an inert solvent such as dioxane, tetrahydrofuran in the presence of an acid such as 4-chloropyridine hydrochloride, or in an acid solvent such as glacial acetic acid, at an elevated temperature, preferably at reflux temperature.

In all these preparations, the reaction products may be isolated from the reaction medium and, if necessary, further purified according to methodologies generally known in the art such as, for example, extraction, crystallization, trituration and chromatography. In particular, stereoisomers can be isolated chromatographically using a chiral stationary phase such as, for example, Chiralpak AD (amylose 3,5 dimethylphenyl carbamate) or Chiralpak AS, both purchased from Daicel Chemical Industries, Ltd, in Japan.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tent-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereoisomeric forms of the compounds and the intermediates of this invention may be obtained by the application of art-known procedures. Diastereomers may be separated by physical separation methods such as selective crystallization and chromatographic techniques, e.g. liquid chromatography using chiral stationary phases. Enantiomers may be separated from each other by the selective crystallization of their diastereomeric salts with optically active acids. Alternatively, enantiomers may be separated by chromato-graphic techniques using chiral stationary phases. Said pure stereoisomeric forms may also be derived from the corresponding pure stereoisomeric forms of the appropriate starting materials, provided that the reaction occurs stereoselectively or stereospecifically. Preferably if a specific stereoisomer is desired, said compound will be synthesized by stereoselective or stereospecific methods of preparation. These methods will advantageously employ chirally pure starting materials. Stereoisomeric forms of the compounds of formula (I) are obviously intended to be included within the scope of the invention.

The chirally pure forms of the compounds of formula (I) form a preferred group of compounds. It is therefore that the chirally pure forms of the intermediates of formula (II), (III) and (VI), their N-oxide forms, their salt forms and their quaternary amines are particularly useful in the preparation of chirally pure compounds of formula (I). Also enantiomeric mixtures and diastereomeric mixtures of intermediates of formula (II), (III) and (VI) are useful in the preparation of compounds of formula (I) with the corresponding configuration.

The compounds of formula (I), the salts, the quaternary amines and the stereochemically isomeric forms thereof are useful agents for combating fungi in vivo. The present compounds are active against a wide variety of fungi, such as *Candida* spp., e.g. *Candida albicans, Candida glabrata, Candida krusei, Candida parapsilosis, Candida kefyr, Candida tropicalis; Aspergillus* spp., e.g. *Aspergillus fumigatus, Aspergillus niger, Aspergillus flavus; Cryptococcus neoformans; Sporothrix schenckii; Epidermophyton floccosum; Microsporum canis: Trichophyton* spp., e.g. *Trichophyton mentagrophytes, Trichophyton rubrum, Trichophyton quinckeanum*; and several dematiaceous hyphomycetes.

In vitro experiments, including the determination of the fungal susceptibility of the present compounds as described in the pharmacological example hereinafter, indicate that the compounds of formula (I) have a favourable intrinsic inhibitory capacity on fungal growth in for instance *Trichophyton rubrum*. Other in vitro experiments such as the determination of the effects of the present compounds on the sterol synthesis in, for instance, *Trichophyton rubrum*, also demonstrate their antifungal potency. Also in vivo experiments in a mouse model show that the present compounds are potent anti fungals when administered intraperitoneally.

In view of the utility of the compounds of formula (I), there is provided a method of treating warm-blooded animals, including humans, suffering from fungal infections. Said method comprises the systemic or topical administration of an effective amount of a compound of formula (I), a N-oxide form, a salt, a quaternary amine or a possible stereoisomeric form thereof, to warm-blooded animals, including humans. Hence, compounds of formula (I) are provided for use as a medicine, in particular, the use of a compound of formula (I) in the manufacture of a medicament useful in treating fungal infections is provided.

The present invention also provides compositions for treating or preventing fungal infections comprising a therapeutically effective amount of a compound of formula (I) and a pharmaceutically acceptable carrier or diluent.

In view of their useful pharmacological properties, the subject compounds may be Formulated into various pharmaceutical forms for administration purposes.

To prepare the pharmaceutical compositions of this invention, a therapeutically effective amount of a particular compound, in base or addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, topically, percutaneously, transungually or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, emulsions, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. As appropriate compositions for topical application there may be cited all compositions usually employed for topically administering drugs e.g. creams, gel, dressings, shampoos, tinctures, pastes, ointments, salves, powders and the like. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

Transungual compositions are in the form of a solution and the carrier optionally comprises a penetration enhancing agent which favours the penetration of the antifungal into and through the keratinized ungual layer of the nail. The solvent medium comprises water mixed with a co-solvent such as an alcohol having from 2 to 6 carbon atoms, e.g. ethanol.

For parenteral compositions, the carrier will usually comprise sterile water, at least in large part. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. For parenteral compositions, also other ingredients, to aid solubility for example, e.g. cyclodextrins, may be included. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermo-dynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps:
a) dissolving the compound of formula (I) and the water-soluble polymer in an appropriate solvent, optionally at elevated temperatures;
b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
a) mixing a compound of formula (I) and an appropriate water-soluble polymer.
b) optionally blending additives with the thus obtained mixture,
c) heating and compounding the thus obtained blend until one obtains a homogenous melt,
d) forcing the thus obtained melt through one or more nozzles; and
e) cooling the melt till it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product can be milled or ground to particles having a particle size of less than 600 μm, preferably less than 400 μm and most preferably less than 125 μm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder The water-soluble polymers in the particles are polymers that have an apparent viscosity, when dissolved at 20° C. in an aqueous solution at 2% (w/v), of 1 to 5000 mPa.s more preferably of 1 to 700 mPa.s, and most preferred of 1 to 100 mPa.s. For example, suitable water-soluble polymers include alkylcelluloses, hydroxyalkyl-celluloses, hydroxyalkyl alkylcelluloses carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses.

Also one or more cyclodextrins can be used as water soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy$C_{1-6}$alkyl, carboxy-$C_{1-6}$alkyl or $C_{1-6}$alkyloxycarbonyl$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$alkyl or carboxy$C_{1-2}$alkyl or more in particular by methyl, ethyl, hydroxyethyl, hydroxypropyl, hydroxybutyl, carboxy-methyl or carboxyethyl. As used hereinbefore, $C_{1-2}$alkyl represents straight or branched chain saturated hydrocarbon radicals having 1 or 2 carbon atoms such as methyl or ethyl; $C_{1-3}$alkyl encompasses the straight and branched chain saturated hydrocarbon radicals as defined in $C_{1-2}$alkyl as well as the higher homologue thereof containing 3 carbon atoms, such as propyl; $C_{2-4}$alkyl represents straight or branched chain saturated hydrocarbon radicals having from 2 to 4 carbon atoms such as ethyl, propyl, butyl, 1-methyl-propyl and the like.

Of particular utility are the β-cyclodextrin ethers, e.g. dimethyl-β-cyclodextrin as described in Drugs of the Future, Vol. 9, No. 8, p. 577–578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another suitable type of substituted cyclodextrins is sulfobutylcyclodextrines.

The ratio of active ingredient over cyclodextrin may vary widely. For example ratios of 1/100 to 100/1 may be applied. Interesting ratios of active ingredient over cyclodextrin range from about 1/10 to 10/1. More interesting ratios of active ingredient over cyclodextrin range from about 1/5 to 5/1.

It may further be convenient to formulate the present benzodiazepine antifungals in the form of nanoparticles which have a surface modifier adsorbed on the surface thereof in an amount sufficient to maintain an effective average particle size of less than 1000 nm. Useful surface modifiers are believed to include those which physically adhere to the surface of the antifungal agent but do not chemically bond to the antifungal agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present antifungals are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and an antifungal agent and a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The pharmaceutical compositions mentioned above may also contain a fungicidally effective amount of other antifungal compounds such as cell wall active compounds. The term "cell wall active compound", as used herein, means any compound which interferes with the fungal cell wall. Appropriate antifungal compounds for use in combination with the present compounds include, but are not limited to, known azoles such as fluconazole, voriconazole, itraconazole, ketoconazole, miconazole, eberconazole, ER 30346, SCH 56592, ZD-0870, UK-292663; squalene epoxidase inhibitors such as terbinafine and butenafine; polyenes such as amphotericin B, nystatin or liposomal and lipid forms thereof, such as Abelcet, AmBisome and Amphocil; purine or pyrimidine nucleotide inhibitors such as flucytosine; polyoxins and nikkomycins, in particular nikkomycin Z or nikkomycin K and others which are described in U.S. Pat. No. 5,006,513 or other chitin inhibitors; elongation factor inhibitors such as sordarin and analogs thereof; mannan inhibitors such as predamycin; bactericidal/permeabilityinducing (BPI) protein products such as XMP.97 or XMP.127; complex carbohydrate antifungal agents such as CAN-296; (1,3)-β-glucan synthase inhibitors including papulacandins, aculeacins, echinocandins (e.g. caspofungin and micafungin); or protegrins such as IB-367.

It is especially advantageous to formulate the aforementioned pharmaceutical compositions in unit dosage form for ease of administration and uniformity of dosage. Unit dosage form as used in the specification and claims herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions, teaspoonfuls, tablespoonfuls and the like, and segregated multiples thereof.

Those of skill in treating warm-blooded animals suffering from diseases caused by fungi could easily determine the therapeutically effective daily amount from the test results given herein. In general, it is contemplated that a therapeutically effective daily amount would be from 0.05 mg/kg to 20 mg/kg body weight.

Experimental Part

A. Preparation of the Intermediates

EXAMPLE A.1

General Procedure for 1-(2-cyanophenyl)pyrrole

A mixture of 2-aminobenzonitrile (0.01 mole), 2,5-dimethoxytetrahydrofuran (0.01 mole) and glacial acetic acid (10 ml) was heated under reflux for 30 minutes (TLC check). The acetic acid and ethyl acetate formed was evaporated off and the residue was purified using flash chromatography on silica gel (eluent: $CH_2Cl_2$). The pure fraction was recrystallized from the appropriate solvent (mostly ethanol).

EXAMPLE A.2

General Procedure for 1-(2-aminomethylphenyl)pyrrole

Method A: Lithium Aluminumhydride Reduction

To a well stirred suspension of (0.05 mol) of lithium alumunium hydride in 100 ml of anhydrous tetrahydrofuran, (0.043 mole) of 1-(2-cyanophenyl)pyrrole were added by small portions. Then the mixture was maintained with stirring at room temperature for 18 hours. Addition of aqueous ethanol to destroy the excess lithium aluminium hydride, followed by filtration afforded a solution, which was then evaporated in vacuo. The residue was extracted with ethyl ether, the organic layer washed with water and dried over anhydrous sodium sulphate. Removal of the solvent under reduced pressure gave a crude product, which was purified by passing through an alumina column eluting with chloroform to give 1-(2-aminomethylphenyl)pyrrole.

Method B: Red-Al® Reduction

To a stilted solution of sodium dihydrobis(2-methoxyethoxy)aluminate (100 ml of 70% w/w solution in toluene) in dry toluene (100 ml) was added dropwise, over one hour, a solution of 1-(2'-cyanophenyl)pyrrole (16.8 g, 0.1 mole) in dry toluene. After 1.5 hours, aqueous sodium hydroxide (10%, 100 ml) was cautiously added. The aqueous layer was separated off and extracted with toluene. The combined organic layers were washed with saturated sodium chloride solution, dried (magnesium sulfate) and evaporated, and the residue vacuum-distilled. The product was converted in its hydrochloride by treatment with iPrOH/HCl solution.

Method C: $KBH_4$/₃COOH Reduction

To a mixture of potassium borohydride (0.55 g, 0.01 mol) and THF (10 ml) a solution of trifluoroacetic acid (1.1 g, 0.01 mol) in THF (1 ml) was added dropwise at a rate so as to keep the reaction temperature between 15–20° C. To the reduction mixture thus obtained a solution of 1-(3-chloro-2-cyanophenyl)pyrrole (0.6 g, 0.003 mol) in THF (15 ml) was added at a rate so as to keep the reaction temperature between 25–30° C. The reaction mixture thus obtained was stirred for further 6 hours at room temperature. Then water (100 ml) was added and the mixture was extracted with $CH_2C_2$ (3×), the organic layer washed with $H_2O$ (2×), NaCl (1×), dried ($MgSO_4$), filtered and evaporated.

The residue was converted to its hydrochloride by treatment with iPrOH/HCl (3 ml) solution. Recrystallisation from iPrOH gave crystals.

Method D: Raney-Nickel Reduction

A mixture of 1-(3-chloro-2-cyanophenyl)pyrrole (16.3 g, 0.08 mol). RaNi (2 g), thiophene (2 ml) in methanol saturated with ammonia (250 ml) was cooled to circa 14° C. and hydrogenated at atmospheric pressure. After uptake of two equivalents of hydrogen, the catalyst was filtered off and the solvent was evaporated. The residue was converted in its hydrochloride by treatment with iPrOH/HCl (16 ml) solution. Besides the aimed product also dehalogenated product was formed as a minor side product.

EXAMPLE A.3

Specific Procedure for 1-(2'-aminomethyl-3'-chlorophenyl)pyrrole

A solution of 2-amino-6-chloro-benzonitrile (30 g), 2,5-dimethoxytetrahydrofuran (30 g) and 4-chloropyridine hydrochloride (17 g) in dioxane was heated to 70° C. for 2.5 h. The solvent was evaporated in vacuo. Dichloromethane was then added to the residue and the spent 4-chloropyridine hydrochloride filtered off. The dichloromethane was evaporated in vacuo to give 1-(3'chloro-2'-cyanophenyl)pyrrole (35 g)

A solution of 1-(3'chloro-2'-cyanophenyl)pyrrole (10 g) in diethyl ether solution was added dropwise to a solution of 1M lithium aluminium hydride in ether solution (100 ml) under nitrogen gas. After addition was complete, the reaction mixture was refluxed for 2 h. and then allowed to stir at room temperature overnight (18 h). The mixture was subsequently quenched with water (4 ml), 2N NaOH (8 ml) and water (16 ml). Stirring was continued for a further 1 h after addition. The crystalline salts were filtered and the filtrate dried over anhydrous magnesium sulphate. After filtering, the ether fitrate was evaporated in vacuo to give the title compound (9.4 g) as a colourless oil.

B. Preparation of the Final Compounds

EXAMPLE B.1

General Procedure

A solution of (0.05 mol) 1-(2-aminomethylphenyl)pyrrole and an aldehyde (0.05 mol) in ethanol (100 ml) was heated under reflux for 4 hours. The solution was evaporated and the residue was dissolved in ether and ethereal hydrogen chloride was added. After stirring for 30 minutes, the precipitate was filtered off and recrystalized from an appropriate alcohol.

EXAMPLE B.2

General Procedure for Alkylation of 7-chloro-5,6-dihydro-4H-pyrrolo[1,2-a][1,4]benzodiazepine A solution of the appropriate alkylhalide (1 mmole) in $CH_3CN$ (5 ml) is added dropwise to a solution of 7-chloro-5,6-dihydro-4H-pyrrolo[1,2-a][1,4]benzodiazepine (1 mmole) and triethylamine (1 mmole) in $CH_3CN$ (5 ml) at room temperature. After stirring at room temperature for 1 to 48 hours, the mixture is evaporated in vacuo and subjected to column chromatography on silica gel.

EXAMPLE B.3

Specific Procedure for 4-(4'-ethylphenyl)-5-methyl-7-chlorobenzo[1,2]-pyrrolo-[1,2a][1,4]diazepine A solution of 1-(2'-aminomethyl-3'-chlorophenyl)pyrrole (1.5 g) and 4-ethylbenzaldehyde (1 g) in ethanol was refluxed 2 h. The solution was cooled to 0° C. and a solution of concentrated (45%) hydrobromic acid (4 ml) in glacial acetic acid (9 ml) was added dropwise. The solution was stirred at room temperature for a further 1 h. after which the compound (2) was filtered off (2.2 g). The compound (2) (0.5 g) was added to a saturated aqueous solution of sodium bicarbonate containing a small quantity of methanol. A slight excess of dimethyl sulphate was added and the reaction mixture stirred at room temperature for 30 minutes. The resulting solid was filtered, dried and purified using a silica gel column using dichloromethane as eluant to give compound (10) (0.17 g) as a white solid.

EXAMPLE B.4

Procedure for Compound 21

A solution of compound (13) was stirred for three days at room temperature in dichloromethane in the presence of an excess of manganese dioxide. The suspension was filtered and the filtrate was purified by column chromatography on silica gel yielding a viscous oil.

EXAMPLE B.5

Procedure for Resolution of (2) into Compounds (24) and (29)

A mixture of 1-(2-aminomethyl-3-chlorophenyl)pyrrole hydrochloride (prepared according to A.2 method D) (0.024 mol) and 4-ethylbenzaldehyde (0.024 mol) in EtOH (50 ml) was stirred and refluxed for 2 hours. The mixture was crystallized overnight. The crystals were filtered off and washed 3 times with EtOH (10 ml) and then cried (vacuum, 60° C.). Yield: 4.7 g The residue was purified by high performance liquid chromatography over Chiralpak AD (eluent: 100% EtOH). The product fractions were collected and the solvent was evaporated. The yield of fraction A (0.968 g) and of fraction B (0.92 g) were converted into the hydrochloric acid salt (1:1) with 2-propanol and HCl (6N), filtered off and dried. Yield: 0.911 g of compound 29 (11.5%) and 0.861 g of compound 24 (11%).

Following the foregoing examples, the following compounds have been prepared.

TABLE 1

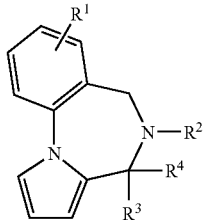

| Comp. No. | $R^1$ | $R^2$ | $R^4$ | $R^3$ | Physical data |
|---|---|---|---|---|---|
| 1 | 7-Cl | H | H | 4-MeO—$C_6H_4$— | .HBr (1:1); m.p.: 242–243° C. |
| 2 | 7-Cl | H | H | 4-Et-$C_6H_4$— | .HBr (1:1); m.p.: 244–245° C. |
| 3 | 7-Cl | H | H | 3-$CF_3$—$C_6H_4$— | .HBr (1:1); m.p.: 226–227° C. |
| 4 | H | H | H | 4-iPr-$C_6H_4$— | .HBr (1:1); m.p.: 251–252° C. |
| 5 | 7-Cl | H | H | 4-Me—$C_6H_4$— | .HBr (1:1); m.p.: 228–229° C. |
| 6 | 7-Cl | H | H | 4-iPr-$C_6H_4$— | .HBr (1:1); m.p.: 338–339° C. |
| 7 | 7-Cl | H | H | 4-tBu-$C_6H_4$— | .HBr (1:1); m.p.: 245–246° C. |
| 8 | 7-Cl | H | H | 4-nBu-$C_6H_4$— | .HBr (1:1); m.p.: 227–228° C. |
| 9 | 7-Cl | H | H | 4-nPr-$C_6H_4$— | .HBr (1:1); m.p.: 238–239° C. |
| 10 | 7-Cl | $CH_3$ | H | 4-Et-$C_6H_4$— | m.p.: 91–92° C. |
| 11 | 8-Cl | H | H | 4-Et-$C_6H_4$— | m.p.: 40–41° C. |
| 12 | 7-Cl | H | H | 3-thienyl | .HBr (1:1); m.p.: 237–238° C. |
| 13 | H | H | H | 4-Et-$C_6H_4$— | .HBr (1:1); m.p 259–260° C. |
| 14 | 7-F | H | H | 4-iPr-$C_6H_4$— | m.p.: 116–118° C. |
| 15 | 7-F | H | H | 4-Et-$C_6H_4$— | m.p.: 133–134° C. |
| 16 | 9-Cl | H | H | 4-Et-$C_6H_4$ | .HBr (1:1); m.p.: 243–244° C. |
| 17 | 9-Cl | H | H | 4-OEt-$C_6H_4$ | .HBr (1:1); m.p.: 248–249° C. |
| 18 | 9-Cl | H | H | 4-iPr-$C_6H_4$ | .HBr (1:1); m.p.; 251–252° C. |
| 19 | 9-Cl | H | H | 4-Me—$C_6H_4$ | .HBr (1:1); m.p.: 244–245° C. |
| 20 | 9-Cl | H | H | 4-CN—$C_6H_4$ | .HBr (1:1); m.p.: 248–249° C. |
| 21 | H | double bond | | 4-Et-$C_6H_4$ | oil |
| 22 | 7-Cl | double bond | | 4-Et-$C_6H_4$ | m.p.: 208–208° C. |

TABLE 1-continued

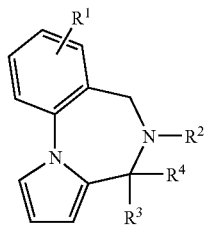

| Comp. No. | R¹ | R² | R⁴ | R³ | Physical data |
|---|---|---|---|---|---|
| 23 | 9-Cl | double bond | | 4-Et-C₆H₄ | m.p.: 124–125° C. |
| 24 | 7-Cl | H | H | 4-Et-C₆H₄ | .HCl (1:1); (B)-isomer; m.p.: 262° C. |
| 25 | 7-Cl | H | H | 3-Et-C₆H₄ | |
| 26 | 7-CH₃ | H | H | 4-Br—C₆H₄ | .HBr (1:1); mp.: 256–257° C. |
| 27 | 7-CH₃ | H | H | 4-Et-C₆H₄ | .HBr (1:1); m.p.: 257–258° C. |
| 28 | 7-CH₃ | H | H | 4-Cl—C₆H₄ | .HBr (1:1); m.p.: 250–251° C. |
| 29 | 7-Cl | H | H | 4-Et-C₆H₄ | .HCl (1:1); (A)-isomer; m.p.: 250° C. |
| 30 | 7-CH₃ | H | H | 4-CH₃S—C₆H₄ | .HBr (1:1); m.p.: 257–258° C. |
| 31 | 7-SCH₃ | H | H | 4-Et-C₆H₄ | .HBr (1:1); m.p.: 239–240° C. |
| 32 | 10-Cl | H | H | 4-Et-C₆H₄ | .HBr (1:1); m.p.: 249–250° C. |
| 33 | 7-OMe | H | H | 4-Et-C₆H₄ | .HBr (1:1); m.p.: 254–255° C. |
| 34 | 7-Cl | H | H | 2-Et-C₆H₄ | |

C. PHARMACOLOGICAL EXAMPLES

EXAMPLE C.1

Measurement of Antifungal Activity In vitro

The test compounds were dissolved at a concentration of $10^{-2}$ M in dimethyl sulfoxide (DMSO) and diluted into CYG broth (Odds, F.C. *Antimicrobial Agents and Chemotherapy* 1992: 36: 1727–1737) to give a final concentration of 10, 3.2, 1, 0.32, 0.1, 0.03, 0.01, 0.003 and 0.00 µM. For some compounds the tests were done at intermediate concentrations. Cultures were inoculated with *Candida kefyr* to an initial concentration of $10^4$/ml and with the other fungal species to an equivalent concentration determined by turbidimetry. Cultures were incubated in the wells of microdilution plates at 37° C. for 48 h (*C. kefyr*) and at 30 C for 5–7 days (*T. rubrum*). Growth in wells containing test compounds was estimated turbidimetrically as a percentage of growth in compound free controls and the lowest concentration of compound that inhibited the growth of an isolate below 35% of control growth was recorded as the lowest active dose (LAD).

EXAMPLE C.2

Determination of Fungal Susceptibility

A panel single isolates of the dermatophytes *Sporothrix schenckii*; *Microsporum canis*; *Trichophyton rubrum*; *Trichophyton mentagrophyte*; *Candida parapsilosis*; *Cryptococcus neoformans*; and *Aspergillus fumigatus* were used to evaluate the activity of the test compounds in vitro. Inocula were prepared as broth cultures (yeasts) or as suspensions of fungal material made from agar slope cultures (moulds). The test compounds were pipetted from dimethylsulfoxide stock solution into water to provide a series of 10-fold dilutions. The fungal inocula were suspended in the growth medium CYG (F.C. Odds, Journal of Clinical Microbiology, 29, 2735–2740, 1991) at approximately 50,000 colony-forming units (CFU) per ml and added to the aqueous test drugs.

The cultures were set up in the 96 wells of plastic microdilution plates and they were incubated for 2 days at 37° C. (*Candida* spp.) or for 5 days at 30° C. (other fungi). Growth in the microcultures was measured by their optical density (OD) measured at a wavelength of 405 nm. The OD for cultures with test compounds was calculated as a percentage of the OD for control cultures, i.e. the OD for cultures without test compounds. Inhibition of growth to 35% of control or less was recorded as significant inhibition.

Minimal inhibitory concentration (MIC; in $10^{-6}$ M) of some of the compounds of formula (I) for the tested species are listed in Table.

TABLE 2a

| | MIC values in $10^{-6}$ M | | |
|---|---|---|---|
| Infection | Comp. 1 | Comp. 2 | Comp. 3 |
| *Sporothrix schenkii* | >10 | >10 | >10 |
| *Microsporum canis* | 5.5 | 0.32 | 2.1 |
| *Trichophyton rubrum* | 2.1 | 0.03 | 2.1 |
| *Trichophyton mentagrophytes* | 2.1 | 0.32 | 3.2 |
| *Candida parapsilosis* | >10 | 1 | >10 |
| *Cryptococcus neoformans* | >10 | >10 | >10 |
| *Aspergillus fumigatus* | 10 | 3.2 | 10 |

TABLE 2b

| | MIC values in $10^{-6}$ M | | |
|---|---|---|---|
| Infection | Comp. 4 | Comp. 5 | Comp. 6 |
| *Sporothrix schenkii* | >10 | >10 | >10 |
| *Microsporum canis* | 10 | 1 | 0.32 |
| *Trichophyton rubrum* | 3.2 | 0.32 | 0.32 |
| *Trichophyton mentagrophytes* | 3.2 | 1 | 1 |
| *Candida parapsilosis* | >10 | >10 | 10 |
| *Cryptococcus neoformans* | >10 | >10 | >10 |
| *Aspergillus fumigatus* | >10 | >10 | >10 |

TABLE 2c

| | MIC values in $10^{-6}$ M | | |
|---|---|---|---|
| Infection | Comp. 7 | Comp. 8 | Comp. 9 |
| *Sporothrix schenkii* | 10 | >10 | >10 |
| *Microsporum canis* | 0.32 | 1 | 0.32 |
| *Trichophyton rubrum* | 0.1 | 0.1 | 0.1 |
| *Trichophyton mentagrophytes* | 1 | 1 | 0.32 |
| *Candida parapsilosis* | 10 | >10 | 3.2 |
| *Cryptococcus neoformans* | >10 | >10 | >10 |
| *Aspergillus fumigatus* | >10 | >10 | >10 |

TABLE 2d

| | MIC values in $10^{-6}$ M | | |
|---|---|---|---|
| Infection | Comp. 10 | Comp. 11 | Comp. 12 |
| *Sporothrix schenkii* | >10 | >10 | >10 |
| *Microsporum canis* | >10 | >10 | >10 |
| *Trichophyton rubrum* | 3.2 | 3.2 | 3.2 |

TABLE 2d-continued

| | MIC values in $10^{-6}$ M | | |
|---|---|---|---|
| Infection | Comp. 10 | Comp. 11 | Comp. 12 |
| Trichophyton mentagrophytes | 10 | 3.2 | >10 |
| Candida parapsilosis | >10 | >10 | >10 |
| Cryptococcus neoformans | >10 | >10 | >10 |
| Aspergillus fumigatus | >10 | >10 | >10 |

TABLE 2e

| | MIC values in $10^{-6}$ M | | |
|---|---|---|---|
| Infection | Comp. 13 | Comp. 14 | Comp. 15 |
| Sporothrix schenkii | >10 | >10 | >10 |
| Microsporum canis | >10 | 10 | 3.2 |
| Trichophyton rubrum | 1 | 0.32 | 0.32 |
| Trichophyton mentagrophytes | 3.2 | 1 | 1 |
| Candida parapsilosis | >10 | >10 | 10 |
| Cryptococcus neoformans | >10 | >10 | >10 |
| Aspergillus fumigatus | >10 | >10 | 10 |

TABLE 2f

| | MIC values in $10^{-6}$ M | | |
|---|---|---|---|
| Infection | Comp. 16 | Comp. 17 | Comp. 18 |
| Sporothrix schenkii | >10 | >10 | >10 |
| Microsporum canis | 1 | >10 | >10 |
| Trichophyton rubrum | 0.1 | 10 | 1 |
| Trichophyton mentagrophytes | 1 | 10 | 1 |
| Candida parapsilosis | >10 | >10 | >10 |
| Cryptococcus neoformans | >10 | >10 | >10 |
| Aspergillus fumigatus | >10 | >10 | >10 |

TABLE 2g

| | MIC values in $10^{-6}$ M | | |
|---|---|---|---|
| Infection | Comp. 19 | Comp. 20 | Comp. 21 |
| Sporothrix schenkii | >10 | >10 | 10 |
| Microsporum canis | 10 | >10 | 0.32 |
| Trichophyton rubrum | 0.32 | 0.32 | 0.03 |
| Trichophyton mentagrophytes | 3.2 | >10 | 0.32 |
| Candida parapsilosis | >10 | >10 | 3.2 |
| Cryptococcus neoformans | >10 | >10 | >10 |
| Aspergillus fumigatus | >10 | >10 | 1 |

D. COMPOSITION EXAMPLE

"Active ingredient" (A.I.) as used throughout these examples relates to a compound of formula (I), a N-oxide, a salt, a quaternary amine or a stereochemically isomeric form thereof.

EXAMPLE D1

Injectable Solution 1.8 Grams methyl 4-hydroxybenzoate and 0.2 grams sodium hydroxide were dissolved in about 0.5 of boiling water for injection. After cooling to about 50° C. there were added while stirring 0.05 grams propylene glycol and 4 grams of the active ingredient. The solution was cooled to room temperature and supplemented with water for injection q.s. ad 1 l, giving a solution comprising 4 mg/ml of active ingredient. The solution was sterilized by filtration and filled in sterile containers.

EXAMPLE D2

Transungual Composition 0.144 g $KH_2PO_4$, 9 g NaCl, 0.528 g $Na_2HPO_4.2H_2O$ was added to 800 ml $H_2O$ and the mixture was stirred. The pH was adjusted to 7.4 with NaOH and 500 mg $NaN_3$ was added. Ethanol (42 v/v %) was added and the pH was adjusted to 2.3 with HCl. 15 mg active ingredient was added to 2.25 ml PBS (Phosphate Buffer Saline)/Ethanol (42%; pH 2.3) and the mixture was stirred and treated with ultrasound. 0.25 ml PBS/Ethanol (42%; pH 2.3) was added and the mixture was further stirred and treated with ultrasound until all active ingredient was dissolved, yielding the desired transungual composition.

EXAMPLE D3

Oral Drops

500 Grams of the A.I. was dissolved in 0.5 l of a sodium hydroxide solution and 1.5 l of the polyethylene glycol at 60~80° C. After cooling to 30~40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE D4

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelatin capsules, comprising each 20 mg of the active ingredient.

EXAMPLE D5

Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams micro-crystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3- propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE D6

2% Cream

Stearyl alcohol (75 mg), cetyl alcohol (20 mg), sorbitan monostearate (20 mg) and isopropyl myristate (10 mg) are introduced in a doublewall jacketed vessel and heated until the mixture has completely molten. This mixture is added to a seperately prepared mixture of purified water, propylene glycol (200 mg) and polysorbate 60 (15 mg) having a temperature of 70 to 75° C. while using a homogenizer for liquids. The resulting mixture is allowed to cool to below 25° C. while continuously mixing. A solution of A.I.(20 mg), polysorbate 80 (1 mg) and purified water q.s. ad 1 g and a solution of sodium sulfite anhydrous (2 mg) in purified water are next added to the emulsion while continuously mixing. The cream is homogenized and filled into suitable tubes.

EXAMPLE D7

2% Cream

A mixture of A.I. (2 g), phosphatidyl choline (20 g), cholesterol (5 g) and ethyl alcohol (10 g) is stirred and heated at 55–60° C. until complete solution and is added to a solution of methyl paraben(0.2 g), propyl paraben (0.02 g), disodium edetate (0.15 g) and sodium chloride (0.3 g) in purified water (ad 100 g) while homogenizing. Hydroxypropylmethylcellulose (1.5 g) in purified water is added and the mixing is continued until swelling is complete.

The invention claimed is:

1. A method for treating a fungal infection in a warm-blooded animal in need thereof comprising administering to the warm-blooded animal a therapeutically effective amount of a compound of the formula

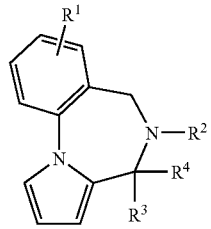

(I)

a N-oxide form, a salt, a quaternary amine or stereochemically isomeric form, wherein
$R^1$ is selected from the group consisting of hydrogen, $C_{1-6}$alkyl, $C_{1-4}$alkylthio, $C_{1-4}$alkyloxy, and halo;
$R^2$ is selected from the group consisting of hydrogen and $C_{1-6}$alkyl;
$R^3$ is selected from the group consisting of 2-thienyl, 3-thienyl and phenyl substituted with a substituent selected from the group consisting of halo, cyano, $C_{1-4}$alkyloxy, $C_{1-4}$alkylthio, $C_{1-6}$alkyl, and haloC$_{1-6}$alkyl; and
$R^4$ is hydrogen; or
$R^2$ and $R^4$ form an extra bond.

2. The method of claim 1 wherein
$R^1$ is selected from the group consisting of hydrogen, $C_{1-6}$alkyl and halo;
$R^2$ is selected from the group consisting of hydrogen and $C_{1-6}$alkyl;
$R^3$ is selected from the group consisting of 2-thienyl, 3-thienyl and phenyl substituted with a substituent selected from the group consisting of halo, cyano, $C_{1-4}$alkyloxy, $C_{1-6}$alkyl, and haloC$_{1-6}$alkyl; and
$R^4$ is hydrogen; or
$R^2$ and $R^4$ form an extra bond.

3. The method of claim 1 wherein
$R^1$ is selected from the group consisting of hydrogen and halo;
$R^2$ is selected from the group consisting of hydrogen and $C_{1-6}$alkyl;
$R^3$ is phenyl substituted with $C_{1-6}$alkyl; and
$R^4$ is hydrogen; or $R^2$ and $R^4$ form an extra bond.

4. The method of claim 1 wherein
$R^1$ is selected from the group consisting of hydrogen, 7-chloro, 7-fluoro and 9-chloro;
$R^2$ is hydrogen;
$R^3$ is phenyl substituted with $C_{1-6}$alkyl; and
$R^4$ is hydrogen; or $R^2$ and $R^4$ form an extra bond.

5. The method of claim 1, provided that $R^3$ is not 4-methylphenyl, 4-methoxyphenyl or 4-isopropylphenyl when $R^1$, $R^2$ and $R^4$ are hydrogen; and $R^3$ is not 4-methoxyphenyl, 4-ethylphenyl or 3-trifluorophenyl when $R^1$ is 7-chloro, and $R^2$ and $R^4$ are hydrogen.

6. A pharmaceutical composition comprising a pharmaceutically acceptable carrier, and as active ingredient a therapeutically effective amount of a compound of the formula (I).

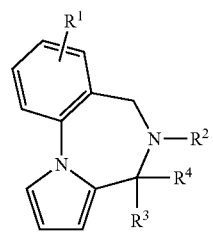

(I)

a N-oxide form, a salt, a quaternary amine or stereochemically isomeric form thereof, wherein
$R^1$ is selected from the group consisting of hydrogen, $C_{1-6}$alkyl, $C_{1-4}$alkylthio, $C_{1-4}$alkyloxy, and halo;
$R^2$ is selected from the group consisting of hydrogen or $C_{1-6}$alkyl;
$R^3$ is selected from the group consisting of 2-thienyl, 3-thienyl and phenyl substituted with a substituent selected from the group consisting of fluro, bromo, iodo, cyano, $C_{1-4}$alkyloxy, $C_{1-4}$alkylthio, $C_{1-6}$alkyl, and haloC$_{1-6}$alkyl; and
$R^4$ is hydrogen; or
$R^2$ and $R^4$ form an extra bond.

7. A process of preparing the pharmaceutical composition of claim 6 comprising intimately mixing a pharmaceutically acceptable carrier with a therapeutically effective amount of the compound of formula (I).

* * * * *